US007928191B2

(12) United States Patent
Minami et al.

(10) Patent No.: US 7,928,191 B2
(45) Date of Patent: Apr. 19, 2011

(54) METHOD FOR PURIFYING BIOACTIVE SUBSTANCES

(75) Inventors: Koichi Minami, Ashigarakami-gun (JP); Yohsuke Takeuchi, Ashigarakami-gun (JP); Taisei Nishimi, Ashigarakami-gun (JP)

(73) Assignee: Fujifilm Corporation, Tokyo (JP)

( * ) Notice: Subject to any disclaimer, the term of this patent is extended or adjusted under 35 U.S.C. 154(b) by 327 days.

(21) Appl. No.: 12/201,594

(22) Filed: Aug. 29, 2008

(65) Prior Publication Data
US 2009/0062515 A1    Mar. 5, 2009

(30) Foreign Application Priority Data
Aug. 29, 2007    (JP) ................. 2007-222064

(51) Int. Cl.
*C07K 1/16*    (2006.01)
(52) U.S. Cl. ........................ 530/344; 530/417
(58) Field of Classification Search .............. None
See application file for complete search history.

(56) References Cited

U.S. PATENT DOCUMENTS

| | | | | |
|---|---|---|---|---|
| 6,087,452 | A * | 7/2000 | Stewart et al. ............. | 525/323 |
| 7,175,767 | B2 | 2/2007 | Andersson et al. | |
| 7,176,298 | B2 | 2/2007 | Tchaga et al. | |
| 2002/0164718 | A1 | 11/2002 | Tchaga et al. | |
| 2006/0199950 | A1 | 9/2006 | Andersson et al. | |
| 2006/0287432 | A1 * | 12/2006 | Christensen et al. ........ | 525/54.2 |
| 2008/0038750 | A1 | 2/2008 | Piehler et al. | |
| 2010/0016564 | A1 * | 1/2010 | Andersson et al. ........... | 530/413 |

FOREIGN PATENT DOCUMENTS

| | | |
|---|---|---|
| WO | 98/06739 A1 | 2/1998 |
| WO | 2004/087284 A1 | 10/2004 |
| WO | 2006/013042 A2 | 2/2006 |

OTHER PUBLICATIONS

Robert, R., et al., "Large-scale production, bacterial localization assessment and immobilized metal affinity chromatography purification of a human single-chain Fv antibody against alphaIIb-beta3 integrin," Int'l J. of Bio. Macromolecules, 39:1-3, Aug. 15, 2006.
Hashim, S.O., et al., "Alkaline active maltohexaose-forming α-amylase from *Bacillus halodurans* LBK 34," Enzyme and Microbial Tech., 36:1, Jan. 6, 2005, 139-146.
Liao, et al., "Novel immobilized metal ion affinity adsorbent based on cross-linked β-cyclodextrin matris for repeated adsorption of α-amylase," Biochem. Engineering J., 23:1, Mar. 1, 2005, 17-24.

(Continued)

*Primary Examiner* — Jeffrey E Russel
(74) *Attorney, Agent, or Firm* — Sughrue Mion, PLLC (57) ABSTRACT

A method for purifying bioactive substances includes the steps of: causing a bioactive substance having histidine units to contact media, each constituted by a substrate, ligands which are physically attached to the surface of the substrate, and Cu(II) or Fe(II) metal ions which are covalently bonded to the ligands; causing the bioactive substance to covalently bond with the metal ions via the histidine units; and washing the media with an amount of 1 nmol/L to 10 mmol/L imidazole derivative solution 60 times the volume of the media or greater. In the case that the metal ions are Cu(II), the bioactive substance which has covalently bonded with the Cu(II) via the histidine units are recovered by one of a 10 mmol/L to 1 mol/L imidazole derivative solution and a 0.5 mmol/L to 5 mol/L EDTA solution.

20 Claims, 2 Drawing Sheets

OTHER PUBLICATIONS

Johnson, R.D. et al., "Multipoint binding in metal-affinity chromatography II. Effect of pH and imidazole on chromatographic retention of engineered histidine-containing cytochromes c," J. of Chromatography, 725:2, Feb. 23, 1996, 225-235.

Suman Lata et al., "Stable and Functional Immobilization of Histidine-Tagged proteins via Multivalent Chelator Headgroups on a Molecular Poly(ethylene glycol) Brush", Analytical Chemistry, Feb. 15, 2005, vol. 77, No. 4, pp. 1096-1105.

* cited by examiner

FIG.2

METHOD FOR PURIFYING BIOACTIVE SUBSTANCES

BACKGROUND OF THE INVENTION

1. Field of the Invention

The present invention is related to a method for purifying bioactive substances.

2. Description of the Related Art

Obtainment of highly pure proteins, which are targets of research, is extremely important in the academic fields such as molecular biology and biochemistry, as well as in the industrial fields such as biochemistry and pharmaceuticals. Recently, utilization of large scale expression systems that employ recombinant genes and host cells to obtain desired proteins as recombined proteins has become possible. A technique that utilizes so called added tags when purifying proteins using the large scale expression systems, is known.

A technique that purifies proteins by employing portions called tags, which are introduced to the N or C ends of proteins that are artificially synthesized by altering genes, is known. A purification method that employs His-tag is a representative example of this technique. His-tag proteins are proteins that have short peptides with six to ten histidine groups attached to the ends thereof. Because the molecular weight of the tag portion is small, there is little effect on the activity or the structure of target proteins. Therefore, His-tag proteins are widely utilized in purification and detection of recombined proteins.

Purification of His-tag proteins which have been expressed by gene recombination is performed by the following steps. A sample that contains the His-tag proteins is caused to flow through a column, thereby causing the His-tag proteins to bond with media. Then, contaminants are washed away by a cleansing liquid. Thereafter, the His-tag proteins are recovered, by causing an eluting solvent to flow over the media. Accordingly, it is necessary for the His-tag proteins to have sufficient bonding force such that they are not washed away by the cleansing liquid. On the other hand, it is necessary for the bonding force of the His-tag proteins to be weakened by the eluting solvent. Conventionally, cleansing is performed using a buffer having the same pH as that when the His-tag proteins are bonded to the media, and recovery of the His-tag proteins is performed using a buffer of a different pH. Alternatively, an eluting solvent containing imidazole is used to elute the His-tag proteins (refer to International Patent Publication No. WO98/06739, for example).

However, it is difficult to perform quantitative purification at high purity levels using this purification technique. A factor in the difficulty is due to the fact that when large amounts of cleansing liquid are utilized to completely purify the His-tag proteins that include contaminants, the His-tag proteins are washed away along with the contaminants.

"Stable and Functional Immobilization of Histidine-Tagged proteins via Multivalent Chelator Headgroups on a Molecular Poly(ethylene glycol) Brush", Anal. Chem., Vol. 77, pp. 1096-1105, 2005 discloses a technique for immobilizing His-tag proteins using NTA-Ni(II) complexes. In this technique, water molecules, which are coordinately bonded to two coordinate sites in each complex, are substituted by nitrogen atoms of two imidazole groups of oligohistidine groups of the His-tag proteins. Thereby, His-tag proteins are caused to specifically bind to the surface of media.

However, His-tag proteins cannot be stably immobilized even if the technique disclosed in "Stable and Functional Immobilization of Histidine-Tagged proteins via Multivalent Chelator Headgroups on a Molecular Poly(ethylene glycol) Brush", Anal. Chem., Vol. 77, pp. 1096-1105, 2005 is applied, if large amounts of cleansing liquid are used. In addition, there is a problem that this technique is not practical from the viewpoint of recovery rates of protein, because the amount of proteins that can be held is small.

SUMMARY OF THE INVENTION

The present invention has been developed in view of the foregoing circumstances. It is an object of the present invention to provide a method for purifying bioactive substances, in which a bioactive substance can be stably bonded even if washed with a large amount of cleansing liquid, and the stably bonded bioactive substance can be easily recovered.

The method for purifying bioactive substances of the present invention comprises the steps of:

causing a bioactive substance having histidine units to contact media, each comprising a substrate, ligands which are physically attached to the surface of the substrate, and metal ions which are covalently bonded to the ligands;

causing the bioactive substance to covalently bond with the metal ions via the histidine units; and washing the media with an amount of 1 nmol/L to 10 mmol/L imidazole derivative solution 60 times the volume of the media or greater;

the metal ions being one of Cu(II) or Fe(II) ions.

It is more preferable for the volume of the imidazole derivative solution to be 100 times or greater than the volume of the media.

It is preferable for the ligands to be nitrilotric acetic acid derivatives.

It is preferable for a hydrophilic polymer to be physically attached to the surface of the substrate; and for the ligands to be held by the hydrophilic polymer.

It is preferable for the ligands to be held by the hydrophilic polymer at a density of $7.8 \times 10^{15}/mm^3$ or greater.

In the case that the metal ions are Cu(II), it is preferable for the bioactive substance which has covalently bonded with the Cu(II) via the histidine units to be recovered by one of a 10 mmol/L to 1 mol/L imidazole derivative solution and a 0.5 mmol/L to 5 mol/L EDTA solution.

In the case that the metal ions are Fe(II), it is preferable for the bioactive substance which has covalently bonded with the Fe(II) via the histidine units to be recovered by a solution containing a reducing agent.

It is preferable for the reducing agent to be at least one of: diothiothreitol; glutathione; cysteine; and β-mercaptoethanol.

It is preferable for the media with which the bioactive substance is in contact to be provided to fill a column.

The method for purifying bioactive substances of the present invention comprises the steps of: causing a bioactive substance having histidine units to contact media, each comprising a substrate, ligands which are physically attached to the surface of the substrate, and metal ions which are covalently bonded to the ligands; and causing the bioactive substance to covalently bond with the metal ions via the histidine units. The metal ions are either Cu(II) or Fe(II). Therefore, it is possible for the bioactive substance to be stably bonded even if the media are washed with a large amount of cleansing liquid. Accordingly, the bioactive substance will not be washed away along with contaminants. In addition, after the bonding of the histidine units, the media are washed with an amount of 1 nmol/L to 10 mmol/L imidazole derivative solution 60 times the volume of the media or greater. Therefore, the bioactive substance can be purified at high purity levels.

In the case that the metal ions are Cu(II), the bioactive substance which has covalently bonded with the Cu(II) via the histidine units is recovered by one of a 10 mmol/L to 1 mol/L imidazole derivative solution and a 0.5 mmol/L to 5 mol/L EDTA solution. In the case that the metal ions are Fe(II), the bioactive substance which has covalently bonded with the Fe(II) via the histidine units is recovered by a solution containing a reducing agent. Thereby, simple quantitative recovery of the bioactive substance is enabled.

BEST MODE FOR CARRYING OUT THE INVENTION

Hereinafter, the method for purifying bioactive substances will be described. First, each component of the media and formation methods (activation methods) thereof will be described. Then, the method for purifying bioactive substances will be described with reference to the attached drawings.

(1) Substrate

The substrate may be of any material as long as it is insoluble in water. Examples of such materials include: cellulose, agarose, dextran, polyacryl amide, silica gel, and porous glass. The substrate is not limited to being planar, and those in the form of beads may also be utilized.

(2) Hydrophilic Polymer

It is preferable for a hydrophilic polymer to be provided on the surface of the substrate, because it is important to suppress contaminants that non specifically adsorb to the substrate in order to perform purification at high purity levels.

(2-1) Hydrophilic Polymer

Examples of hydrophilic polymers that can be utilized in the present invention include: gelatin; agarose; chitosan; dextran; carrageenan; arginine; starch; cellulose; derivatives thereof, such as carboxymethyl derivatives; and water swelling organic polymers, such as: polyvinyl alcohol; polyacrylic acid; polyacryl amide; polyethylene glycol; and derivatives thereof.

Further, It is possible to use carboxymethyl group containing synthetic polymers and carboxymethyl group containing polysaccharides as the hydrophilic polymer in the present invention. Examples of carboxymethyl group containing synthetic polymers include: polyacrylic acid; polymethacrylic acid; and copolymers of polyacrylic acid and polymethacrylic acid. Examples of such copolymers include: methacrylic acid copolymers as disclosed in Japanese Unexamined Patent Publication Nos. 59(1984)-053836 (page 3, line 20—page 6, line 49) and 59(1984)-071048 (page 3, line 41—page 7, line 54); acrylic acid copolymers; itaconic acid copolymers; crotonic acid copolymers; maleic acid copolymers; partially esterified maleic acid copolymers; and polymers having hydroxyl groups, to which anhydrides are added. Examples of carboxylmethyl group containing polysaccharides include: natural plant extracts; products of microbial fermentation; synthetics formed by enzymes; and chemically synthesized compositions. Specific examples include: hyaluronic acid; chondroitin sulfate; heparin; dermatan sulfate; carboxymethyl cellulose; carboxyethyl cellulose; cellouronic acid; carboxymethyl chitin; carboxymethyl dextran; and carboxymethyl starch. Commercially available compounds may be used as the carboxymethyl group containing polysaccharides. Examples of such commercially available compounds include: CMD, CMD-L and CMD-D40 (manufactured by Meito Sangyo Co., Ltd.), which are carboxymethyl dextrans; carboxymethylcellulose sodium (manufactured by Wako Pure Chemical Industries, Ltd.), and sodium arginine (manufactured by Wako Pure Chemical Industries, Ltd.).

The molecular weight of the hydrophilic polymers containing carboxyl groups to be used in the present invention is not particularly limited. It is preferable for the molecular weight of the hydrophilic polymer to be within a range from 200 to 5,000,000. It is more preferable for the molecular weight of the hydrophilic polymer to be within a range from 100,000 to 2,000,000.

(2-2) Activation of the Hydrophilic Polymer

In the case that a polymers that contain carboxyl groups are utilized as the hydrophilic polymer, the polymer can be immobilized onto the substrate by activating the carboxyl group. Known techniques can be used to activate the polymers containing carboxyl groups. Examples of such methods include: a method in which carboxyl groups are activated using 1-(3-Dimethylaminopropyl)-3 ethylcarbodiimide (EDC), which is a water soluble carbodiimide, and N-Hydroxysuccinimide (NHS); and a method in which carboxyl groups are activated using EDC alone. The hydrophilic polymer can be immobilized on the substrate, by causing the polymers containing the carboxyl groups, which have been activated by these methods, to react with the substrate, which has amino groups.

Another method for activating polymers that contain carboxyl groups is that which employs nitrogenous compounds. Specifically, nitrogenous compounds having the chemical structures illustrated by General Formula Ia and General Formula Ib below may be employed. In General Formula Ia and General Formula Ib, $R^1$ and $R^2$ represent carbonyl groups, carbon atoms, or nitrogen atoms, each of which can have independently substituted groups. $R^1$ and $R^2$ may form five member rings or six member rings by covalent bonding. A represents a carbon atom having a substituted group or a phosphor atom having a substituted group. M represents a (n−1) valent element. X represents a halogen atom.

Here, $R^1$ and $R^2$ represent carbonyl groups, carbon atoms, or nitrogen atoms, each of which can have independently substituted groups. Preferably, $R^1$ and $R^2$ form five member rings or six member rings by covalent bonding. Particularly preferred examples of such five member rings or six member rings are: hydroxysuccinic acid; hydroxyphthalic acid; 1-hydoxybenzo triazole; 3,4-dihidroxy-3-hydroxy-4-oxo-1,2,3-benzotriazine; and derivatives thereof.

Alternatively, the nitrogenous compounds represented by the following chemical formulae may be employed.

As preferred nitrogenous compounds, those that are represented by General Formula I below may be employed. In General Formula I, Y and Z represent CH or a nitrogen atom, independently from each other.

(I)

Preferred examples of the specific compounds represented by General Formula I are indicated below.

The following compound is another example of a nitrogenous compound.

As a further alternative, compounds represented by General Formula II below may be employed as the nitrogenous compound. In General Formula II, A represents a carbon atom having a substituted group or a phosphor atom having a substituted group; Y and Z represent CH or a nitrogen atom, independently from each other; M represents a (n−1) valent element; and X represents a halogen atom.

Here, it is preferable for the substituted group of the carbon atom or the phosphor atom to be an amino group having a substituted group. Dialkyl amino groups, such as dimethyl amino groups and pyrrolidinone groups are preferred. Examples of the (n−1) valent element represented by M include a phosphor atom, a boron atom, and an arsenic atom, with phosphor being the preferred (n−1) valent element. Examples of the halogen atom represented by X include a fluorine atom, a chlorine atom, a bromine atom, and an iodine atom, with fluorine being the preferred halogen atom.

Preferred examples of the specific compounds represented by General Formula II are indicated below.

As a still further alternative, compounds represented by General Formula III below may be employed as the nitrogenous compound. In General Formula III, A represents a carbon atom having a substituted group or a phosphor atom having a substituted group; M represents a (n−1) valent element; and X represents a halogen atom.

A preferred example of a specific compound represented by General Formula III is indicated below.

As another method for activating the polymer containing the carboxyl group, phenol derivatives having electron withdrawing groups may be utilized. It is preferable for the δ value of the electron withdrawing group to be 0.3 or greater. Specifically, compounds represented by the following formulae may be employed.

Further, carbodiimide derivatives may be used in conjunction in methods for activating polymers containing carboxyl groups. Preferably, water soluble carbodiimide derivatives may be used. (1-ethyl-3-(3-dimethylaminopropyl)carbodiimide, hydrochloride), represented by the following chemical formula, may be used.

In addition to the above carbodiimide derivative, nitrogenous compounds and phenol derivatives may also be used in conjunction, or independently, as desired. A combination of a carbodiimide derivative and a nitrogenous compound is preferred.

The compound represented by the following chemical formula may also be used to activate polymers containing carboxyl groups. The compound may be used singly, or used in combination with a carbodiimide derivative, a nitrogenous compound, or a phenol derivative.

Further, the technique described in paragraphs [0011] through [0022] of Japanese Unexamined Patent Publication No. 2006-058071 may be used to activate carbonic acids of polymers containing carboxyl groups. In this technique, carbonic acid amide groups are formed by activating carboxyl groups which are present on the surface of a substrate with uronium salt, phosphonium salt, or triazine derivatives having specific structures. As another alternative, the technique described in paragraphs [0011] through [0019] of Japanese Unexamined Patent Publication No. 2006-090781 may be used to activate carbonic acids of polymers containing carboxyl groups. In this technique, carboxyl groups which are present on the surface of a substrate are activated with a carbodiimide derivative or a salt thereof. Then, the activated carboxyl groups are esterified by a nitrogenous heteroaromatic compound having a hydroxy group, a phenol derivative having an electron withdrawing group, or an aromatic compound having a thiole group. The esterified carboxyl groups are caused to react with an amine to form carbonic acid amide groups.

Note that the uronium salt, phosphonium salt, and triazine derivatives having specific structures disclosed in Japanese Unexamined Patent Publication No. 2006-058071 are uronium salts represented by General Formula 1, phosphonium salts represented by General Formula 2, and triazine derivatives represented by General Formula 3 below.

Formula 1

Formula 2

Formula 3

In General Formula 1, $R^1$ and $R^2$ each independently represent an alkyl group having a carbon number of 1 to 6, or represent an alkylene group having a carbon number of 2 to 6 together, that forms a ring with the N atom; $R^3$ represents an aromatic ring group having a carbon number of 6 to 20, or a heterocyclic ring having at least one heteroatom; and X— represents an anion. In General Formula 2, $R^4$ and $R^5$ each independently represent an alkyl group having a carbon number of 1 to 6, or represent an alkylene group having a carbon number of 2 to 6 together, that forms a ring with the N atom; $R^6$ represents an aromatic ring group having a carbon number of 6 to 20, or a heterocyclic ring having at least one heteroatom; and X— represents an anion. In General Formula 3, $R^7$ represents an onium group, and $R^8$ and $R^9$ each represents an electron donor group.

(3) Ligands

Various chelate solutions may be used as compounds to become the ligands. Preferred examples include polydentate ligands, such as: a nitrilotriacetic acid derivative (NTA (N-(5-amino-1-carboxypentyl)iminodiacetic acid)); iminodiacetic acid; phenanthroline; terpyridine; bipyridine; triethylene tetraamine; bi(ethylene triamine); tris(carboxy methyl) ethylene diamine; diethylene triamine pentaacetic acid; polypyrazolyl boric acid; 1,4,7-triazacyclononane; dimethyl glyoxime; and diphenyl glyoxime. Among these, NTA, which is a quadridentate ligand, is preferred. In the case that the hydrophilic polymer having carboxyl groups is provided on the surface of the substrate, the ligands can be immobilized onto the hydrophilic polymer, by activating the carboxyl groups, then causing a compound which is to become the ligand to react therewith, for example.

Note that in the case that the hydrophilic polymer is not provided on the surface of the substrate, the ligands may be caused to bond directly to the substrate, or to a backing layer (a layer formed by hydrophilic polymers such as polyvinyl alcohol or hydrophobic polymers such as epoxy resin). The surface of the substrate itself may be activated by plasma irradiation, UV irradiation, ozone exposure or the like. Then, the ligands may be immobilized onto the surface of the substrate either directly or via a backing layer.

In the case that the hydrophilic polymer is provided on the surface of the substrate, it is preferable for the ligands to be held by the hydrophilic polymer at a density of $7.8 \times 10^{15}/mm^3$ or greater. An organic solvent is employed during bonding of the ligands. Use of the organic solvent enables bonding of the ligands at a density of $7.8 \times 10^{15}/mm^3$ or greater. Examples of organic solvents include: dimethylsulfoxide; N,N-dimethylformamide; N,N-dimethylacetoamide; acetonitrile; N-methylpyrrolidone; acetone; methyl ethyl ketone; methanol; ethanol; isopropyl alcohol; sec-butyl alcohol; tert-butyl alcohol; butyl cellosolve; tetrahydrofuran; and diglyme. From the viewpoints, of solubility of reactive groups and suppression of side reactions, dimethylsulphoxide and N,N-dimethyl formamide are preferred.

Note that in the present specification, each medium may be of a structure in which the metal film, the self assembled monolayer, the hydrophilic polymer, and the ligands are provided on the substrate in this order. In this structure, the metal film and the self assembled monolayer are not strictly necessary. The substrate, the metal film, and the self assembled monolayer will be described below.

(Substrate)

In the case that use in a surface plasmon resonance biosensor is considered, materials which are transparent with respect to laser beams may be utilized as the material for the substrate of the biosensor chip. Examples of such materials include: optical glass, such as BK7; and synthetic resin, such as polymethyl methacrylate, polyethylene terephthalate, polycarbonate, and cycloolefin polymer. It is desirable for the substrate to be formed by a material that does not exhibit anisotropy with respect to polarization, and is superior in workability.

(Metal Film)

It is preferable for the metal film to be physically attached to the substrate. Here, "physically attached to the substrate" includes cases in which the metal film is physically attached to the substrate via another layer, that is, without directly contacting the substrate, in addition to cases in which the metal film is in direct contact with the substrate. The metal to be utilized as the material of the metal film is not particularly limited, as long as it is capable of generating surface plasmon resonance. However, it is preferable for the material to be at least one metal, selected from a group consisting of: gold, silver, bronze, platinum, palladium, and aluminum. Gold is particularly preferred. These metals may be used singly or in combination. In addition, a layer of chrome, for example, may be interposed between the substrate and the metal film.

The thickness of the metal film may be set as desired. However, if the medium is used in a surface plasmon resonance biosensor, it is preferable for the thickness of the metal film to be within a range from 0.1 nm to 500 nm, and more preferably within a range from 1 nm to 200 nm. This is because surface plasmon phenomena of media cannot be sufficiently detected if the thickness of the metal film exceeds 500 nm. In the case that the layer of chrome or the like is interposed between the substrate and the metal film, the thickness of the interposed layer is preferably within a range from 0.1 nm to 10 nm.

(Self Assembled Monolayer)

Self assembled monolayers refer to ultrathin films, such as monomolecular films and LB films, which have uniform regularity imparted by the mechanism of the film material, without external control being exerted. Self assembled monolayers enable formation of uniformly regular structures and patterns over long distances under non equilibrial conditions.

It is preferable for the self assembled monolayer to be formed by a compound represented by a general chemical formula X—R—Y. Here, X is a group which is capable of covalently bonding with the metal film. Specific examples of such groups include: —SH, —SS, —SeH, —SeSe, and —COSH. R is a divalent organic linking group, and ma be interrupted by a heteroatom. Preferably, R is a straight (non branching) chain to enable dense packing. R may be a hydrocarbon chain that includes double and/or triple bonds. Carbon chains may be hyper fluorinated, if necessary. It is preferable for the carbon number of the alkyl chain length of R to be within a range from 2 to 8. Y is a group which is capable of bonding with the hydrophilic polymer, NTA, or the like. Specifically, Y represents a functional group selected from among a group consisting of a hydroxy carbonyl group, an alkoxy group, and an alkyl group.

More specifically, preferred examples of molecules that form the self assembled monolayer are: alkanethiols for metal surfaces; alkylsilanes for glass surfaces, and alcohols for silicon surfaces. Specific examples of alkanethiols include: 7-carboxy-1-heptanethiol; 10-carboxy-1-decanethiol; 4,4'-dibutyl dithio acid; 11-hydroxy-1-undecanethiol. Specific examples of alkylsilanes include: aminopropyl trimethoxysilane; aminoethyl aminotriethoxy silane; and hydroxypropyl triethoxy silane.

(4) Bioactive Substance

Examples of the bioactive substance include: immunoproteins; enzymes; microorganisms; nucleic acids; low molecular weight organic compounds; anti-immunoproteins; immunoglobulin binding proteins; glycobinding proteins; sugar chains that recognize sugars; fatty acids; fatty acid esters; polypeptides having ligand binding potential; and oligopeptides having ligand binding potential. These bioactive substances have histidine units, and are immobilized on the substrate by coordinate bonding with Cu(II) or Fe(II), which are metal ions, via the histidine units. It is preferable for the number of histidine units to be three or greater. To achieve stronger bonds, it is more preferable for the number of histidine units to be six or greater, and further preferable for the number of histidine units to be within a range from 10 to 100.

(5) Purification of Bioactive Substances

In the case that the media to be used in the method for purifying bioactive substances of the present invention is provided with the hydrophilic polymer on the surface of the substrates thereof, ligands are caused to bond with the hydrophilic polymer, and Cu(II) or Fe(II) is caused to contact and bond with the ligands, to form the media. When a solution that contains a bioactive substance is caused to contact the ligands of the media, the histidine units of the bioactive substance bond with the carboxyl groups of the ligands.

Figure 1:
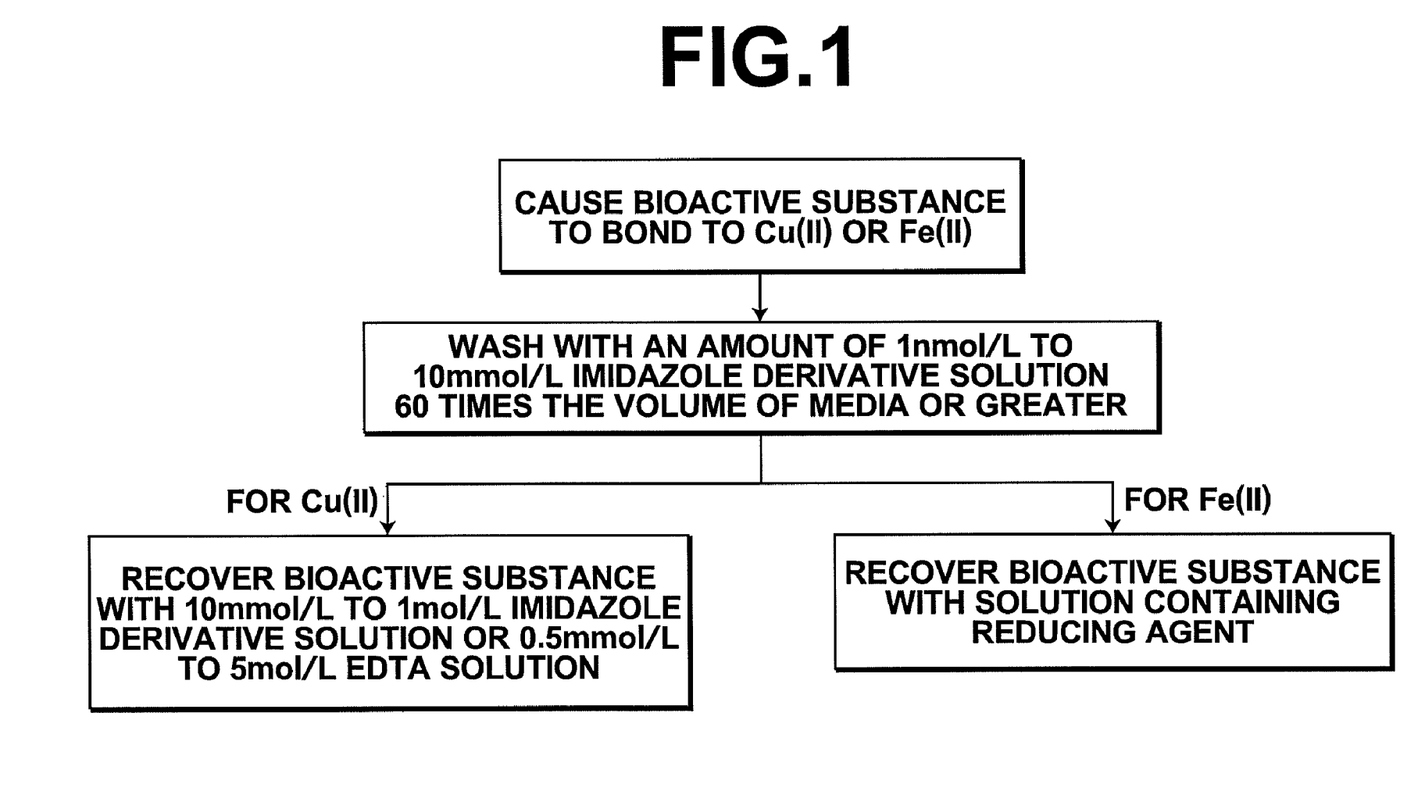
FIG. 1 is a diagram that illustrates the steps of the method for purifying bioactive substances of the present invention.

Hereinafter, a description will be given with reference to FIG. 1. FIG. 1 is a diagram that illustrates the steps of the method for purifying bioactive substances of the present invention. After the bioactive substance is bonded to the media, the surfaces of the media to which the bioactive substance is bonded are washed with an amount of an imidazole derivative solution 60 times the volume of the media or greater, and preferably 100 times the volume of the media or greater. Here, "60 times the volume of the media or greater" and "100 times the volume of the media or greater" means 60 times the volume of a column which is filled with the media or greater, and 100 times the volume of a column which is filled with the media or greater. The concentration of the imidazole derivative solution is within a range from 1 nmol/L to 10 mmol/L. Preferably, the concentration of the imidazole derivative solution is within a range from 100 nmol/L to 10 mmol/L, and more preferably within a range from 100 nmol/L to 1 mmol/L.

Contaminants can be completely removed from the surfaces of the media, by washing with the great amount of the imidazole derivative solution. On the other hand, the bioactive substance does not separate from the media even when the media are washed with the great amount of imidazole derivative solution, because they are strongly bonded to the media. Accordingly, quantitative purification of the bioactive substance at high purity levels is enabled.

The purified bioactive substance is recovered. In the case that the metal ions are Cu(II), it is preferable for the bioactive substance which has covalently bonded with the Cu(II) via the histidine units to be recovered by a 10 mmol/L to 1 mol/L imidazole derivative solution or a 0.5 mmol/L to 5 mol/L EDTA solution.

In the case that the metal ions are Fe(II), it is preferable for the bioactive substance which has covalently bonded with the Fe(II) via the histidine units to be recovered by a solution containing a reducing agent. Diothiothreitol; glutathione; cysteine; and β-mercaptoethanol may be used as the reducing agent either singly or in combination. The concentration of the reducing agent in the solution varies depending on the reducing agent which is used. Generally, however, it is preferable for the concentration of the reducing agent in the solution to be within a range from 100 μM to 20 mM, and more preferably within a range from 500 μM to 10 mM.

Figure 2:
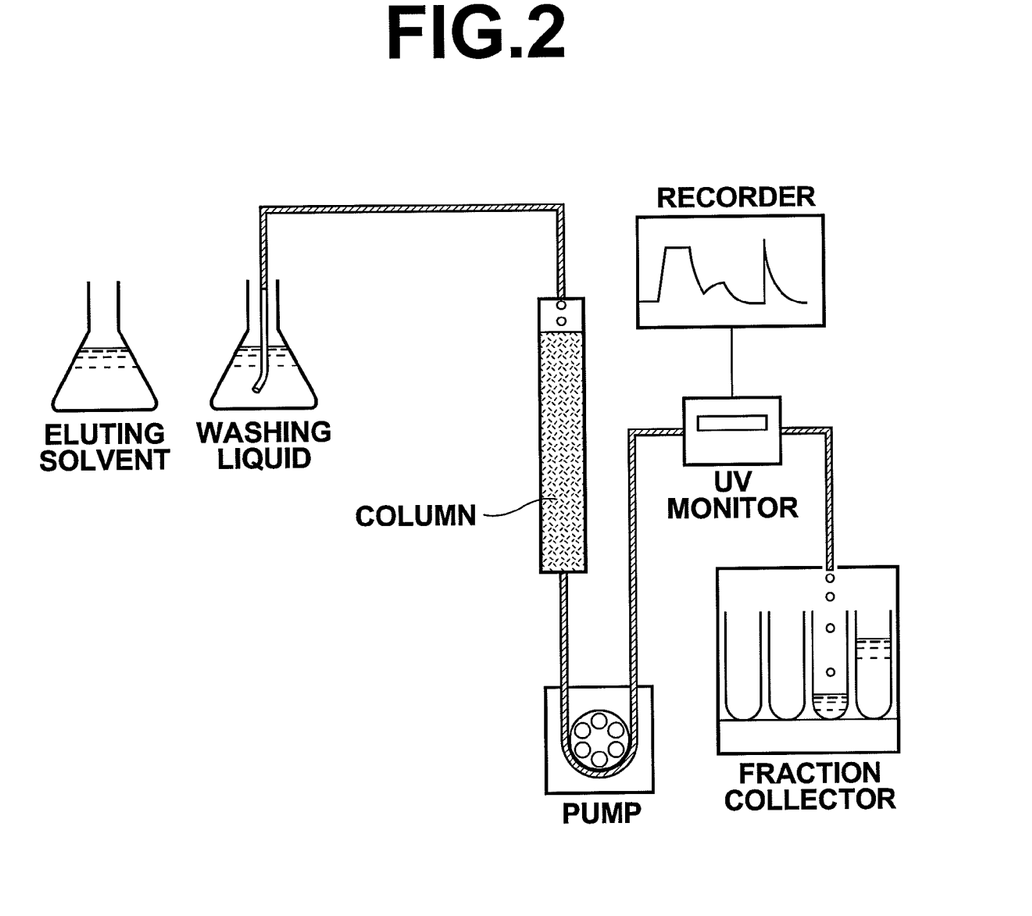
FIG. 2 is a schematic diagram that illustrates an apparatus employed in column chromatography.

Next, the method for purifying bioactive substances of the present invention will be described in the case that media to which a bioactive substance has been placed in contact are filled in a column with reference to FIG. 2. FIG. 2 is a schematic diagram that illustrates an apparatus employed in column chromatography. A column is filled with media. Each medium is constituted by: a substrate; a hydrophilic polymer provided on the surface of the substrate; ligands which are bonded to the hydrophilic polymer; and metal ions which are bonded to the ligands. A bioactive substance is caused to contact and bond with the media. A pump, for causing a cleansing liquid and an eluting solvent to flow through the column at appropriate speeds, is connected to the column. A fraction collector, for recovering liquids which have passed through the column, is connected to the other end of the pump. A UV monitor, for monitoring elution of the bioactive substance by changes in UV absorption, is provided between the pump and the fraction collector. A recorder, for recording changes in UV, is connected to the UV monitor.

Note that here, a case is described in which the column is filled with media to which the bioactive substance has been bonded. Alternatively, the bioactive substance may be caused to contact media that fills the column.

An amount of the cleansing liquid 60 times the volume of the media or greater is caused to flow over the media that fill the column, and the pump is driven to cause contaminants that remain in the column to flow out. The liquid that flows out through the column is collected in the fraction collector as a non adsorption fraction (Fraction 1). Thereafter, the pump is driven to cause the eluting solvent to flow through the column. The liquid that flows out through the column is collected in the fraction collector as an adsorption fraction (Fraction 2). In the case that the bioactive substance is a protein, the bioactive substance can be recovered by causing the eluting solvent to flow until the absorption of 280 nm UV decreases to background levels, as monitored by the UV monitor. The results of purification can be analyzed by measurement of absorption of a light beam having a wavelength of 280 nm using a spectral photometer for each fraction, electrophoresis of each fraction, and measurement of activity for each fraction. According to the method for purifying bioactive substances of the present invention, no bioactive substance will be found in Fraction 1, and highly pure bioactive substances will be quantitatively recovered in Fraction 2.

Note that an example has been described in which a column is filled with the media. However, the purification method of the present invention is not limited to column chromatography. The purification method of the present invention may be applied to biosensors constituted by receptor sites that recognize chemical substances as detection targets, and transducer sites that convert physical or chemical changes at the receptor sites into electric signals. The purification method of the present invention may also be employed in conjunction with the surface plasmon resonance (SPR) measuring technique, the quartz crystal microbalance (QCM) measuring technique, a technique that utilizes the functional surfaces of gold colloid particles to superfine particles, and the like.

For example, a surface plasmon resonance biosensor is constituted by a member having a portion that transmit and reflect light irradiated thereon from a sensor, and a portion on which bioactive substances are immobilized. The media that fills the column may be employed as the portion on which the bioactive substances are immobilized. In this case, the substrate may be changed to that formed by a plate (made of optical glass, such as BK7; or synthetic resin, such as polymethyl methacrylate, polyethylene terephthalate, polycarbonate, and cycloolefin polymer) which is transparent with respect to laser beams, on which a metal film (gold, silver, copper, platinum, palladium, aluminum, and the like) is provided.

Hereinafter, Examples of the purification method of the present invention will be described.

Example 1

(1) Active Esterification of CMD

CMD (by Meito Sangyo Co. Ltd., molecular weight: 1,000,000) was dissolved in ultrapure water such that the concentration thereof was 0.5 weight %. Then, a 0.4M EDC (1-(3-dimethylaminopropyl)-3-ethylcarbodiimide) and 0.1M NHS (N-hydroxysuccinimide) solution was added to the CMD solution and stirred for five minutes at room temperature. The amounts of EDC and NHS are calculated to cause 2% of carboxyl groups to be activated in the case that the entire amount thereof undergoes a reaction.

(2) Immobilization of CMD onto Substrate

The activated esterified CMD solution was caused to react with EAH Sepharose 4B (by Pharmacia Biotech, Inc, 7-11 μmol/ml amino group concentration in swollen gel) using the method described in Affinity Chromatography Principles and Methods (Pharmacia Biotech) to immobilize the CMD onto the substrate.

(3) Formation of AB-NTA Film

The carboxyl groups of the CMD were activated, by adding 50 μl of a solution, which was obtained by adding 0.2 mmol of EDC and 0.04 mmol of NHS to 1 ml of DMSO, to 100 ml of the substrates to which CMD has been immobilized. The substrates were left in the solution for 30 minutes at room temperature. Then, the solution was removed, and the substrates were washed with DMSO. Thereafter, the substrates were caused to react with a solution, which was obtained by adding 0.1 mmol of AB-NTA (by Dojindo Chemicals) to 1 ml of DMSO, for 12 hours. Thereafter, the solution was removed, and the substrates were washed once with ultrapure water.

(Measurement of the Number of Ligands)

A 0.1 mol/L $NiCl_2$ solution was added to the substrates for 10 minutes and then removed. The substrates were washed twice with ultrapure water. Two extractions were performed with 5 ml of a 50 mmol/L EDTA solution. The extracted liquids were combined and measured with an ICP analyzing apparatus. Ni was detected at a concentration of 0.07 ppm. The number of ligands was calculated from the amount of Ni and the volume of the media.

(Purification of Enzymes)

20 ml of a 1 mmol/L copper sulfate solution was added to 5 ml of the substrates, to which the AB-NTA film has been formed as described in (3), and shaken for 30 minutes. Thereafter, the substrates were washed with 300 ml of ultrapure water. Further, 1 ml of a 1:1 mixture of a 10 nmol/L His6-GFP solution and a 10 nmol/L Avidin-FITC solution was added to the substrates, and shaken for 30 minutes. The media, to which the His6-GFP were bonded in this manner, were filled in the column (column volume: 5 ml) illustrated in FIG. 2, then washed with 500 ml of a 0.1 mmol/L imidazole solution. Thereafter, 20 ml of a 10 mmol/L imidazole solution was added to recover the His6-GFP, and the effluent fraction was batched off. The purity and recovery rate of the His6-GFP in the batched off fraction were calculated by UV-Vis spectral measurement (using 8453 by Agilent) and fluorescent measurement (using PHERAStar by EMGLABTECH).

Example 2

Preparation of the media and purification of His6-GFP were performed in the same manner as in Example 1, except that 1 mmol of EDC and 0.2 mmol of NHS were used to activate the carboxyl groups instead of 0.2 mmol of EDC and 0.04 mmol of NHS, and that 300 ml of a 10 mmol/L imidazole solution was used to wash the media instead of 500 ml of the 0.1 mmol/L imidazole solution.

Example 3

Preparation of the media and purification of His6-GFP were performed in the same manner as in Example 1, except that a 1 nmol/L ferrous (II) chloride solution was used instead of the 1 mmol/L copper sulfate solution, and that 500 ml of a 1 mmol/L β-mercaptoethanol solution was used to wash the media instead of 500 ml of the 0.1 mmol/L imidazole solution.

Example 4

Preparation of the media and purification of His6-GFP were performed in the same manner as in Example 1, except that 500 ml of a 10 mmol/L imidazole solution was used to wash the media instead of 500 ml of the 0.1 mmol/L imidazole solution.

Comparative Example 1

20 ml of a 2 mmol/L cobalt (II) chloride solution was added to 10 ml of the media formed according to (3) of Example 1, then shaken for 30 minutes. Further, 1 ml of a 1:1 mixture of a 10 nmol/L His6-GFP solution and a 10 nmol/L Avidin-FITC solution was added to the substrates, and shaken for 30 minutes. The media obtained in this manner were filled in the column, then washed with 500 ml of a 0.01 mmol/L imidazole solution. Thereafter, a 100 mmol/L imidazole solution was added to recover the His6-GFP, but no His6-GFP was able to be recovered.

Comparative Example 2

20 ml of a 2 mmol/L nickel (II) chloride solution was added to 10 ml of the media formed according to (3) of Example 1, then shaken for 30 minutes. Then, the media were washed with 300 ml of ultrapure water. Further, 1 ml of a 1:1 mixture of a 10 nmol/L His6-GFP solution and a 10 nmol/L Avidin-FITC solution was added to the substrates, and shaken for 30 minutes. The media obtained in this manner were filled in the column, then washed with 250 ml of a 1 mmol/L imidazole solution. His6-GFP was found to have eluted into the washing liquid.

Measurement results of the purity and recovery rates for the Examples and the Comparative Examples are illustrated in Table 1 below.

TABLE 1

| | Metal Ion | Ligand Density (number/mm$^3$) | Washing Liquid, Amount (ratio with respect to media volume) | Eluting Solvent | Purity (%) | Recovery Rate (%) |
|---|---|---|---|---|---|---|
| Example 1 | $Cu^{2+}$ | $7.8 \times 10^{15}$ | 0.1 mmol/L Imidazole Solution 500 ml (100x) | Imidazole Solution 100 mmol/L | 95 | 90 |
| Example 2 | $Cu^{2+}$ | $1.5 \times 10^{17}$ | 10 mmol/L Imidazole Solution 300 ml (60x) | Imidazole Solution 100 mmol/L | 95 | 90 |

TABLE 1-continued

|  | Metal Ion | Ligand Density (number/mm³) | Washing Liquid, Amount (ratio with respect to media volume) | Eluting Solvent | Purity (%) | Recovery Rate (%) |
|---|---|---|---|---|---|---|
| Example 3 | $Fe^{2+}$ | $7.8 \times 10^{15}$ | 10 mmol/L Imidazole Solution 500 ml (100x) | β-mercaptoethanol Solution 10 mmol/L | 80 | 75 |
| Example 4 | $Cu^{2+}$ | $8.0 \times 10^{15}$ | 10 mmol/L Imidazole Solution 500 ml (100x) | Imidazole Solution 100 mmol/L | 90 | 80 |
| Comparative Example 1 | $Co^{2+}$ | $7.9 \times 10^{15}$ | 0.01 mmol/L Imidazole Solution 500 ml (100x) | Imidazole Solution 100 mmol/L | — | 0 |
| Comparative Example 2 | $Ni^{2+}$ | $7.8 \times 10^{15}$ | 1 mmol/L Imidazole Solution 250 ml (50x) | — | — | 0 |

As can be clearly seen from the results illustrated in Table 1, the purification method of the present invention enables bioactive substances to be held stably, even if great volumes of low concentration imidazole solution are used to wash media. Therefore, purification can be performed at high purity, and bioactive substances can be recovered at high yields by high concentration imidazole solutions or solutions containing reducing agents.

Note that steps similar to those of the Examples were used to purify His6-GFP from 0.1 of egg white, to which 1 ml of a 10 nmol/L His6-GFP solution was added.

What is claimed is:

1. A method for purifying bioactive substances, comprising the steps of:
    causing a bioactive substance having histidine units to contact media, the media comprising a substrate, ligands which are physically attached to the surface of the substrate, and metal ions which are covalently bonded to the ligands;
    causing the bioactive substance to covalently bond with the metal ions via the histidine units; and
    washing the media with an amount of 1 nmol/L to 10 mmol/L imidazole solution or 1 nmol/L to 10 mmol/L imidazole derivative solution 60 times the volume of the media or greater;
    the metal ions being one of Cu(II) or Fe(II) ions.

2. The method for purifying bioactive substances as defined in claim 1, wherein:
    the volume of the imidazole solution or the imidazole derivative solution is 100 times or greater than the volume of the media.

3. The method for purifying bioactive substances as defined in claim 1, wherein:
    the ligands are nitrilotriacetic acid derivatives.

4. The method for purifying bioactive substances as defined in claim 2, wherein:
    the ligands are nitrilotriacetic acid derivatives.

5. The method for purifying bioactive substances as defined in claim 1, wherein:
    a hydrophilic polymer is physically attached to the surface of the substrate; and
    the ligands are held by the hydrophilic polymer.

6. The method for purifying bioactive substances as defined in claim 2, wherein:
    a hydrophilic polymer is physically attached to the surface of the substrate; and
    the ligands are held by the hydrophilic polymer.

7. The method for purifying bioactive substances as defined in claim 3, wherein:
    a hydrophilic polymer is physically attached to the surface of the substrate; and
    the ligands are held by the hydrophilic polymer.

8. The method for purifying bioactive substances as defined in claim 4, wherein:
    a hydrophilic polymer is physically attached to the surface of the substrate; and
    the ligands are held by the hydrophilic polymer.

9. The method for purifying bioactive substances as defined in claim 5, wherein:
    the ligands are held by the hydrophilic polymer at a density of $7.8 \times 10^{15}/mm^3$ or greater.

10. The method for purifying bioactive substances as defined in claim 6, wherein:
    the ligands are held by the hydrophilic polymer at a density of $7.8 \times 10^{15}/mm^3$ or greater.

11. The method for purifying bioactive substances as defined in claim 7, wherein:
    the ligands are held by the hydrophilic polymer at a density of $7.8 \times 10^{15}/mm^3$ or greater.

12. The method for purifying bioactive substances as defined in claim 8, wherein:
    the ligands are held by the hydrophilic polymer at a density of $7.8 \times 10^{15}/mm^3$ or greater.

13. The method for purifying bioactive substances as defined in claim 1, wherein:
    the metal ions are Cu(II); and
    the bioactive substance which has covalently bonded with the Cu(II) via the histidine units is recovered by one of a 10 mmol/L to 1 mol/L imidazole derivative solution, 10 mmol/L to 1 mol/L imidazole solution, and a 0.5 mmol/L to 5 mol/L EDTA solution.

14. The method for purifying bioactive substances as defined in claim 3, wherein:
    the metal ions are Cu(II); and
    the bioactive substance which has covalently bonded with the Cu(II) via the histidine units is recovered by one of a 10 mmol/L to 1 mol/L imidazole derivative solution, 1 nmol/L to 10 mmol/L to 1 mol/L imidazole solution, and a 0.5 mmol/L to 5 mol/L EDTA solution.

15. The method for purifying bioactive substances as defined in claim 5, wherein:
    the metal ions are Cu(II); and
    the bioactive substance which has covalently bonded with the Cu(II) via the histidine units is recovered by one of a 10 mmol/L to 1 mol/L imidazole derivative solution, 10 mmol/L to 1 mol/L imidazole solution, and a 0.5 mmol/L to 5 mol/L EDTA solution.

16. The method for purifying bioactive substances as defined in claim 1, wherein:

the metal ions are Fe (II); and the bioactive substance which has covalently bonded with the Fe (II) via the histidine units is recovered by a solution containing a reducing agent.

17. The method for purifying bioactive substances as defined in claim 3, wherein:

the metal ions are Fe (II); and the bioactive substance which has covalently bonded with the Fe (II) via the histidine units is recovered by a solution containing a reducing agent.

18. The method for purifying bioactive substances as defined in claim 5, wherein:

the metal ions are Fe (II); and the bioactive substance which has covalently bonded with the Fe (II) via the histidine units is recovered by a solution containing a reducing agent.

19. The method for purifying bioactive substances as defined in claim 16, wherein:

the reducing agent is at least one selected from the group consisting of dithiothreitol; glutathione; cysteine; and β-mercaptoethanol.

20. The method for purifying bioactive substances as defined in claim 1, wherein:

the media with which the bioactive substance is in contact are filled in a column.

* * * * *